United States Patent [19]

Zimmerman

[11] Patent Number: 4,994,467

[45] Date of Patent: Feb. 19, 1991

[54] TREATING AUTISM AND OTHER DEVELOPMENTAL DISORDERS IN CHILDREN WITH NMDA RECEPTOR ANTAGONISTS

[76] Inventor: Andrew W. Zimmerman, 930 Emerald Ave., Ste. 815, Knoxville, Tenn. 37917

[21] Appl. No.: 359,115

[22] Filed: May 31, 1989

[51] Int. Cl.$^5$ ...................... A61K 31/12; A61K 31/44
[52] U.S. Cl. ................................... 514/284; 514/288; 514/676
[58] Field of Search ........................ 514/284, 288, 676

[56] References Cited

U.S. PATENT DOCUMENTS 3,932,623  1/1976  Wilson ................................. 424/177
4,778,794  10/1988  Narus et al. ......................... 514/254

*Primary Examiner*—Stanley J. Friedman
*Attorney, Agent, or Firm*—Luedeka, Hodges & Neely

[57] ABSTRACT

A method is provided for treating autism and other pervasive developmental disorders in children by the administration of a therapeutically effective amount of a N-methyl-D-aspartate (NMDA) receptor antagonist. The NMDA receptor antagonist is chosen from the group consisting of ketamine and dextromethorphan.

7 Claims, No Drawings

TREATING AUTISM AND OTHER DEVELOPMENTAL DISORDERS IN CHILDREN WITH NMDA RECEPTOR ANTAGONISTS

The present invention relates to methods for the treatment of autism and other pervasive developmental disorders in children by means of the administration of an effective amount of a pharmaceutical.

Thousands of children suffer from the effects of pervasive developmental disorders. In addition, thousands of parents and other relatives must provide care for those children. Those children who suffer from the severest forms of these disorders must now be institutionalized. This institutionalization imposes a large expense on the families of the children and on society for the care of those children.

Various diagnostic terms, including atypical symbiotic psychosis, childhood psychosis, childhood schizophrenia and others, have been used to describe these disorders in the past. Though some early investigators suggested that these disorders were continuous with adult psychoses (e.g., schizophrenia), substantial research suggests that they are unrelated to those disorders, although autism itself may continue into adulthood.

In some cases, the disorder apparently follows a period of relatively normal social development in the first five years of life; but even in early childhood, there is invariably failure to develop cooperative play, imaginative play or friendships. As the child grows older, however, a greater awareness of, and social interests in, others may develop. Some of the least handicapped may eventually reach a stage in which they can become passively involved in other children's games or physical play, or include other children as mechanical aids in their own stereotyped activities.

The Diagnostic and Statistical Manual of Mental Disorders, Third Edition-Revised (DSM-III-R) has characterized pervasive developmental disorders by the qualititative impairment of a child (1) in the development of reciprocal social interactions, (2) in the development of verbal and nonverbal communication skills and imaginative activity and (3) in the often markedly restricted repertoire of activities and interests, which frequently is stereotyped and repetitive. The severity and expression of these impairments vary greatly from child to child.

The qualitative impairment of a child in reciprocal social interactions is characterized by a failure to develop interpersonal relationships as well as a lack of responsiveness to, or interest in, people. In infancy these deficiencies may be shown by a failure to cuddle, by lack of contact and facial responsiveness and by indifference or aversion to affection and physical contact. Adults may be treated as interchangeable or the child may cling mechanically to a specific person. The attachment of some toddlers to their parents may be bizarre, e.g., a child may seem to recognize his mother primarily on the basis of smell.

There may also be an impairment in communication and in imaginative activity which includes both verbal and nonverbal skills. Language may be totally absent. When it develops, it is often characterized by immature but essentially normal grammatical structure, delayed or immediate echolalia (repetition of what is said), pronoun reversal, inability to name objects, inability to use abstract terms, idiosyncratic utterances whose meaning is clear only to those who are familiar with the child's past experiences and abnormal speech melody, such as question-like rises at ends of statements or monotonous tone of voice. Nonverbal communication, e.g., facial expression and gesture, may be absent or, if present, is socially inappropriate in form. Likewise, an impairment in imaginative activity may also be evident. This impairment may include the absence of symbolic or fantasy play with toys or the absence of playacting of adult roles. Additionally, imaginative activity may be restricted in content and repetitive and stereotyped in form. This is in marked contrast to the varied content of normal "pretend" play.

Finally, there is a markedly restricted repertoire of activities and interests in a child with a pervasive developmental disorder. This restriction may take various forms. In the younger child, there may be resistance or even catastrophic reactions to minor changes in the environment, e.g., the child may scream when his or her place at the dinner table is changed. There is often obsessive attachment to objects, such as a string or rubber band. Motor repetitions may include hand-clapping, peculiar hand movements, rocking and dipping and swaying movements of the whole body. In an older child there may be an insistence on following routines in a precise way, e.g., throwing a tantrum if the same route to a favorite restaurant is not followed. Verbal stereotypic actions include repetition of words or phrases regardless of meaning. In older children, tasks involving long-term memory, for example, recall of the exact words of songs heard years before, historical dates, or chemical formulae, may be excellent, but the information tends to be repeated over and over again, regardless of the social contacts and the appropriateness of the information.

The most severe form of pervasive developmental disorder is the autistic disorder, also known as infantile autism or Kanner's syndrome. Autism is typically evident at birth with early signs that include an absence of social smiling, a failure to seek or anticipate being picked up or a failure in molding to the individual holding the child. The three most reliable characteristics of an autistic individual are (1) an inability to relate to others, (2) specific language deficits and (3) a concern for the maintenance of homeostasis or sameness. A rare subtype of autistic individuals comprises those with extraordinary intellectual capabilities in specific areas (also known as idiot savants).

A wide variety of treatment interventions for autism have been attempted over the years, but there have been no significant advances in the treatment of this disorder. Those treatments that have been tried generally address the symptoms of the disease rather than the causes.

It is accordingly an object of the present invention to provide a safe method for treating autism and other pervasive developmental disorders in children. It is a further object to produce improvements in behavior without dangerous side effects. Various other objects and advantages will be apparent from the following description.

Generally, in accordance with the present invention, autism and other pervasive developmental disorders in children are treated by the use of a N-methyl-D-aspartate (NMDA) receptor antagonist in a therapeutically effective amount. The NMDA receptor antagonist is preferably selected from the group consisting of ketamine and dextromethorphan. The NMDA receptor antagonist is administered by intravenous or intramuscular injection, rectally via suppository or orally. The NMDA receptor antagonist is administered in an anesthetic dose of ketamine over a period ranging from 60–120 minutes or in a subanesthetic dose of dextromethorphan continuously administered over a period of more than two weeks.

Ketamine and ketamine hydrochloride are dissociative anesthetics with rapid onset and short duration. They produce amnesia and analgesia while maintaining muscle tone. There are minimal effects on respiratory activity. Unlike conventional anesthetic agents, ketamine does not act primarily on the reticular activating system in the brain stem but rather it is thought to act on the cortex and the limbic system. An adult awakening from the ketamine anesthesia may suffer hallucinations but the drug seems to be well tolerated by children and is approved for their use by the FDA. It is often used in combination with nitrous oxide for the induction of anesthesia. Its lack of effect on the functional residual capacity is a distinctive feature in children.

Without being bound by the theory, it is believed that ketamine may be increasing (or disinhibiting) activity in the limbic system pathways in the brain of children with autism. These children may have been previously damaged (or inhibited) in this area which then results in the autistic behavior patterns. It may be that there is a modification of the NMDA receptor in children with autism, probably at the gene control level. This gene may fail to down-regulate. There are probably a variety of causes for the gene failure, since autism itself can result from a variety of known, as well as unknown, causes.

Dextromethorphan and dextromethorphan hydrobromide are used as antitussive agents, i.e., they are used in suppressing the cough reflex. The drug is used for the temporary relief caused by minor bronchial irritation such as may occur with common colds or with inhaled irritants. Dextromethorphan is most effective in the treatment of chronic, nonproductive coughs. It is a common ingredient in commercial cough mixes available without prescription. Dextromethorphan has a low order of toxicity, with a low potential for toxic effects following acute overdosage. Dextromethorphan preparations are usually administered orally in either lozenges, chewable pieces, or solution.

The mechanism of dextromethorphan in suppressing coughs is not well known. However, it has been shown, like ketamine, that dextromethorphan is an antagonist of the NMDA receptor. Again, without being bound by the theory, it is believed that the mechanism of dextromethorphan as used in the treatment of pervasive developmental disorders is similar to that of ketamine.

The invention will be better understood from the following examples which are given by way of illustration and not by way of limitation.

EXAMPLE 1

Patients received ketamine anesthesia administered both intramuscularly and intravenously according to Table I. The ketamine hydrochloride was in a 5% dextrose solution and was administered as 40 mg injected intramuscularly over less than one minute followed by 200 mg injected in an intravenous drip over 2 hours. The effect of the anesthesia lasted about 1 hour after the intravenous drip was discontinued but the improvement in behavior lasted from five to fifteen days after the administration of the anesthesia.

Patient A was calm over two days and then became gradually and increasingly upset with frequent crying as was her base line. The beneficial effects lasted approximately five days after the anesthesia. Patient B was somewhat lethargic on the first day following the administration of the ketamine but by the second day he was alert, calmer and had a marked decrease in self-abusive behavior. Within ten days of the administration of the ketamine, patient B had learned two new words: "Night-Night" and "bathroom." The improvement lasted for a period of twelve days. Patient C became more alert and responsive during the two week period following the administration of the ketamine. No sideeffects were seen in any of the patients.

TABLE I

| Patient | Sex | Age (yrs) | Weight (kg) | Amount of Ketamine (mg)[1] | |
|---|---|---|---|---|---|
| | | | | IM[2] | IV[2] |
| A | Female | 4 | 15 | 40 | 200 |
| B | Male | 8 | 23 | 40 | 200 |
| C | Male | 6 | 18 | 40 | 200 |

[1] in 5% dextrose, IM over a period of less than one minute, IV over a period of about 2 hours.
[2] IM is intramuscular; IV is intravenous.

EXAMPLE 2

Patients received dextromethorphan orally in BENYLIN ® DM (Parke-Davis) according to Table II. The patients received a dosage of 10 mg of dextromethorphan in 5 mL of BENYLIN ® DM three or four times a day over a period of several weeks. Improved behavior was seen in all patients.

After 6 weeks of treatment, patient D showed a marked improvement in language skills and a decrease in general agitation and hyperactivity. She also showed a decreased difficulty in sleeping at night. After 5 weeks of treatment, patient E showed a general decrease in hyperactivity and a general increase in attention span. He is still somewhat resistive when examined but he can be worked with. After two weeks of treatment, patient F was alert and seemed calm. She has interacted with others and has been using words and brief phrases. In an enclosed examining room, she made fewer circulating movements, she stood still, she played with a toy for 30 to 60 seconds and she did not avoid an examination. She still showed some hyperactivity but, in general, she also showed a marked improvement in behavior.

TABLE II

| Patient | Sex | Age (Yr) | Weight (kg) | Amount Per Day | |
|---|---|---|---|---|---|
| | | | | BENYLIN ® DM[1] (mL) | Dextromethorphan (mg) |
| D | Female | 7 | 25.0 | 20 | 40 |
| E | Male | 9 | 64.6 | 20 | 40 |
| F | Female | 5 | 18.6 | 15 | 30 |

[1] BENYLIN ® DM (Parke-Davis): 10 mg dextromethorphan in 5 mL of solution, with 100 mg Guaifenesen.

It may be seen from the foregoing that the treatment of autistic children with a single dose of NMDA receptor antagonist such as ketamine produced improvements in behavior lasting from five to fifteen days, long after the anesthetic effects wore off. The improved behavior included increased incidence of eye contact, decreased incidence of self-abusive behavior, increased calmness and an increase in linguistic ability. In addition, the treatment with oral subanesthetic doses of dextromethorphan also produced dramatic improvements in behavior. The continuous dosage of about 20 mg/12 hr of NMDA receptor antagonist produced improvements in the behavior of the children treated and those improvements remained stable over a period of weeks.

This is a marked improvement in the treatment of autism in children. Previously, the victims of autism were institutionalized where their behavior and desire for sameness were convenient for the caretakers of the children. In addition, previous improvements in the behavior of autistic children were often based on a combination of luck and intensive work on the part of the caretakers. As is shown above, the administration of ketamine and dextromethorphan produces surprisingly and consistently improved behavior in these children without the intensive work previously required.

Therefore, the present invention provides a safe method for treating autism and other pervasive developmental disorders in children without dangerous side effects.

While preferred embodiments have been described in the foregoing detailed description, it will be recognized that there is no intent to limit the invention by such disclosure, but rather it is intended to cover all modifications and variations falling within the spirit and scope of the invention as defined in the appended claims.

What is claimed is:

1. A method of treating autism and other pervasive developmental disorders in children comprising the administration to said children of a therapeutically effective amount of a N-methyl-D-aspartate receptor antagonist chosen from the group consisting of ketamine, a pharmaceutically acceptable salt thereof, dextromethorphan and a pharmaceutically acceptable salt thereof.

2. The method of claim 1 wherein said antagonist is chosen from the group consisting of ketamine and a pharmaceutically effective salt thereof.

3. The method of claim 2 wherein said antagonist is administered intramuscularly and intravenously.

4. The method of claim 3 wherein about 40 mg of said antagonist is administered intramuscularly over a period of time of less than about 1 minute and about 200 mg of said antagonist is administered over a period of time of from about 90 minutes to about 120 minutes.

5. The method of claim 1 wherein said antagonist is chosen from the group consisting of dextromethorphan and a pharmaceutically effective salt thereof.

6. The method of claim 5 wherein said antagonist is administered orally.

7. The method of claim 6 wherein said antagonist is administered in a dose of from about 0.5 mg/kg to about 3.0 mg/kg of body weight per day.

* * * * *